(12) United States Patent
Richardson

(10) Patent No.: US 11,779,379 B2
(45) Date of Patent: Oct. 10, 2023

(54) STERNUM FIXATION DEVICES AND METHODS

(71) Applicant: CircumFix Solutions, Inc., Piperton, TN (US)

(72) Inventor: Kenneth Walter Richardson, Collierville, TN (US)

(73) Assignee: CircumFix Solutions, Inc., Piperton, TN (US)

( * ) Notice: Subject to any disclaimer, the term of this patent is extended or adjusted under 35 U.S.C. 154(b) by 215 days.

(21) Appl. No.: 17/353,011

(22) Filed: Jun. 21, 2021

(65) Prior Publication Data

US 2021/0393306 A1    Dec. 23, 2021

Related U.S. Application Data

(60) Provisional application No. 63/134,406, filed on Jan. 6, 2021, provisional application No. 63/041,807, filed on Jun. 19, 2020.

(51) Int. Cl.
*A61B 17/82* (2006.01)
*A61B 17/88* (2006.01)
*A61B 17/80* (2006.01)

(52) U.S. Cl.
CPC ........ *A61B 17/823* (2013.01); *A61B 17/8076* (2013.01); *A61B 17/8861* (2013.01)

(58) Field of Classification Search
CPC ... A61B 17/82; A61B 17/823; A61B 17/8076; A61B 17/8861
See application file for complete search history.

(56) References Cited

U.S. PATENT DOCUMENTS

| 11,241,264 | B2 * | 2/2022 | Houff | A61B 17/8061 |
| 2011/0106153 | A1 | 5/2011 | Stone et al. | |
| 2014/0155895 | A1 | 6/2014 | McClellan et al. | |
| 2015/0366593 | A1 * | 12/2015 | Mebarak | A61B 17/8014 |
| | | | | 606/281 |
| 2019/0099207 | A1 | 4/2019 | Houff | |
| 2020/0078063 | A1 | 3/2020 | Garcia et al. | |

FOREIGN PATENT DOCUMENTS

JP    2005137757 A    6/2005

OTHER PUBLICATIONS

PCT/US2021/038246 International Search Report and Written Opinion, dated Oct. 13, 2021, 13 pages.

* cited by examiner

*Primary Examiner* — Si Ming Ku
(74) *Attorney, Agent, or Firm* — Nelson Mullins Riley & Scarborough LLP

(57) ABSTRACT

A sternum fixation device includes a plate having a first end and a second end, a right lateral edge and a left lateral edge, an inner side configured for placement against the sternum, and an outer side. A first lobe includes a band socket defined as a blind recess in the outer side of the plate. The band socket includes a right lateral stop and a left lateral stop opposite the right lateral stop. A right lateral channel is defined in the first lobe from the right lateral edge to the band socket, the right lateral channel defined above a right side floor in the socket. A left lateral channel opposite the right lateral channel is defined in the first lobe from the left lateral edge to the band socket, the left lateral channel defined above a left floor in the socket.

17 Claims, 14 Drawing Sheets

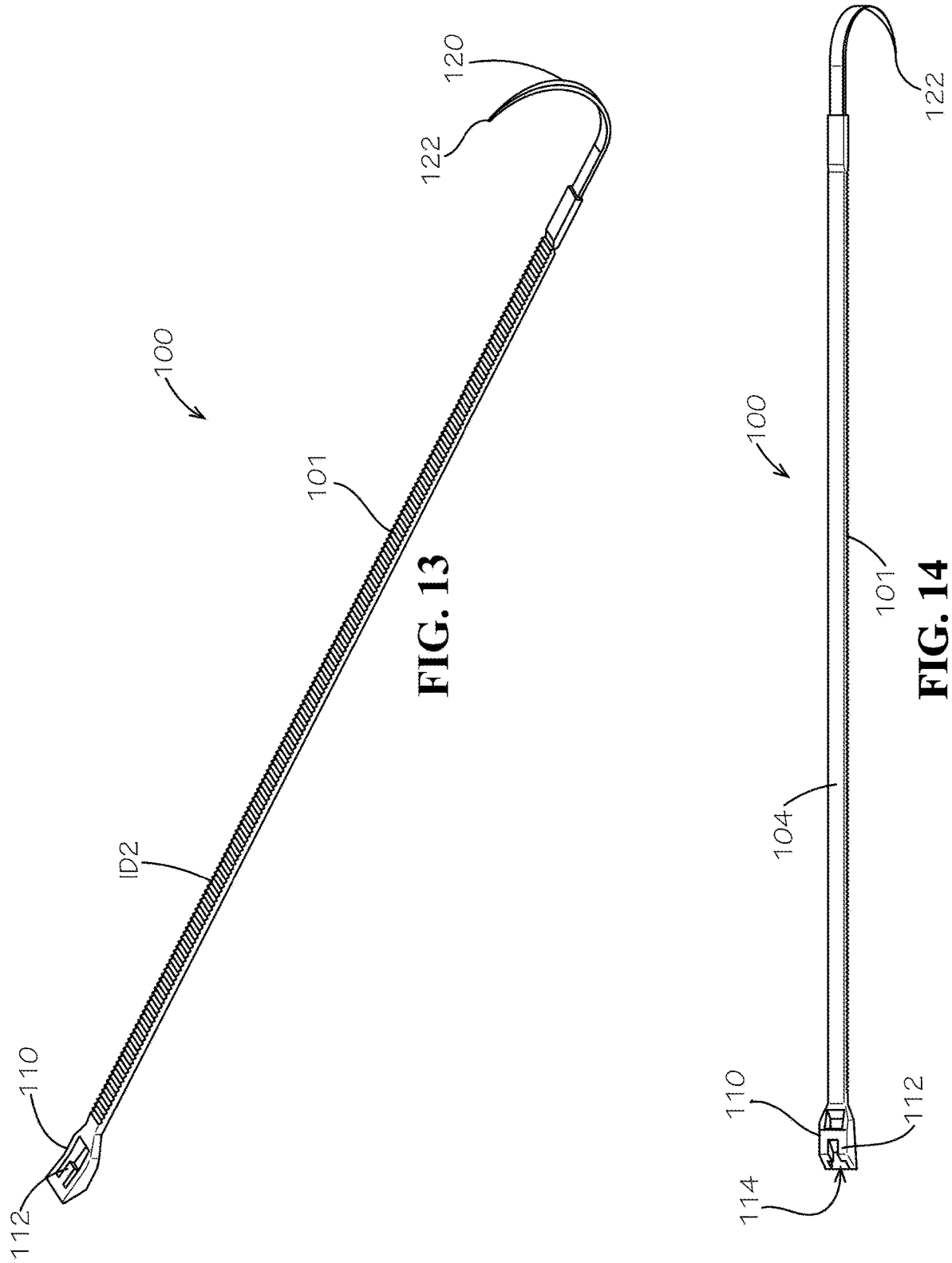

STERNUM FIXATION DEVICES AND METHODS

CROSS-REFERENCES TO RELATED APPLICATIONS

This non-provisional patent application claims priority to and benefit of earlier-filed provisional patent application No. 63/134,406 filed Jan. 6, 2021 titled "Keyed Locking Band and Plate Assembly" and also provisional patent application No. 63/041,807 filed Jun. 19, 2020 titled "Sternum Fixation Device and Method" all of which are hereby incorporated by reference in their entireties.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH DEVELOPMENT

None.

REFERENCE TO SEQUENCE LISTING OR COMPUTER PROGRAM LISTING APPENDIX

None.

BACKGROUND

The present invention relates to devices and methods for securing bone and more particularly to devices and methods for sternum fixation to aid in the healing of a fractured sternum or a split sternum as the result of an osteotomy.

Over the last 30 years Open Reduction Internal Fixation (ORIF) with Rigid Internal Fixation (RIF) has become accepted as the standard of care for treating many types of fractures helping patients painlessly return to pre-injury function earlier and more reliably than conventional treatment methods such as casting, bracing and interosseous or cerclage wiring. In addition, when properly applied, RIF improves the reestablishment of pre-fracture anatomical bone alignment promoting more reliable infection free healing. Besides the proven benefits in trauma care, ORIF is an acceptable method of repositioning bones in elective procedures and repairing bones surgically cut or fractured when necessary to gain surgical access to perform a primary procedure. Such is the case in open-heart surgery where the sternum is surgically cut to gain access to cardiovascular structures contained within the chest wall. In such cases the sternum is surgically cut along the midline of the long axis of the bone separating the sternum and the associated rib cage in half sections left and right The standard method for reconstructing the surgically cut sternum is the placement of stainless steel wires circumferentially (cerclage) around the sternum segments and compressing together by twisting the wires tight to hold the surgically cut bone ends together approximating the pre-cut anatomical position of the sternum and chest wall. In most cases wire fixation has proven to be a successful and cost effective method of repairing the cut sternum with minimal reports of infection and non-union. The literature describes complication rates (infection and/or non-union) as high as 8%. Patients that incur complications, however, endure significant pain and resolving their issues has proven difficult, time consuming, and expensive.

Patients with certain underlying health issues are predisposed to complications and a delayed healing response. For instance, perhaps most significantly, certain cardiovascular patients with multiple health issues including, as examples, COPD, diabetes, and/or suppressed immune response that may delay or prevent healing, exhibit a propensity for post-operative infection, hardware failure and/or nonunion of the sternum. Other factors, such as age, poor diet, smoking, alcohol abuse and/or drug use, can also adversely affect healing. Many of these patients exhibit diseased bone that is weak and may lack sufficient cortical density and thickness.

Over the years, numerous attempts have been made to improve a method for fixing the sternum, but most devices are designed to address the sternum after complications have arisen and are not intended to prevent complications by providing an improved primary solution. Furthermore, many of the commonly marketed products tend to be over engineered, complicated and time-consuming to implant. There are also a host of devices that do not appropriately address the complexities of the human anatomy and the demands such fixation must address in clinical application. Those devices tend to offer no benefit over wire fixation and may lead to unexpected and unintended complications beyond what is known from wire fixation.

The sternum is a flat bone with a thin cortex shell (dense outer bone layer). Cortical density and thickness are important factors with screw fixation techniques as they provide resistance against pullout when screws are tightened as purchase is achieved by the threads compacting and resting in bone. Cortical density and thickness are also important factors in cerclage wire fixation as stability relies on wires compressing directly against the cortex to maintain secure fixation.

An implant construct must provide and maintain sufficient stabilization for a duration long enough to allow bone healing to occur. If healing does not occur within an acceptable timeframe, hardware loosening often leading to hardware failure becomes an increasing risk. This principle also applies to sternum fixation. In the patient population prone to delayed healing and increased risk of complication, cerclage wire fixation may be contraindicated. In such cases, fixation failure occurs due to broken or loosened wires. In some instances, such wire (loosen by cutting through the sternum cortex (commonly referred to as the "cheese grater effect"), which leads to mobility of the bone fragments, potential fracture of the sternum, and almost certain infection. Frequently when patients exhibit failed cerclage wire fixation, radical debridement of soft tissue and bone is necessary and subsequent reconstruction resembles a salvage procedure.

Coughing, which is a very common post-operative occurrence, especially with patients with COPD or pneumonia, generates high peak forces that act on the repaired sternum, thus increasing the incidence of failure of cerclage wire, as well.

Uncontrolled motion between two fractured bone fragments may also contribute to an increased incidence for infection. As such, the fixation construct chosen must control motion under functional loading conditions to create a favorable healing situation. Opinions have varied over the years as to how much rigidity is desirable in a fixation construct. Historically, it was considered a treatment goal to create a motion-free interface between two bone fragments which can be achieved by compressing the fractured or severed bone surfaces in direct opposition, eliminating all motion and encouraging direct healing without the formation of a callus. However, it has now been realized, through the passage of time and the gaining of valuable experience in this area, that the need for extreme rigidity, and thus the elimination of all motion in this situation, is not necessary for the prevention of callus formation. In essence, it has been found that fixation constructs that are substantially more rigid than the bones they are holding can lead to a condition known as stress shielding that fosters poor bone quality and strength giving rise to potential secondary complications including re-fracture. Load-sharing by implants is increasingly gaining favor as it is thought to promote healthier and stronger bone.

Another consideration is whether fixation implants can and should be left in the body long-term or permanently. There are many factors to consider such as patient age, the anatomical location of the implant, and the difficulty in removal. Generally, however, most surgeons prefer to leave fixation implants in vivo permanently and not perform a secondary procedure for removal whenever possible. Many cases of fixation implant removal result from patient complaints of discomfort, irritation, and palpability. An ideal implant design is one that can be left in permanently and causes little or no pain or discomfort to the patient during the healing phase and beyond.

The implant material is another major consideration in making the best implant fixation choice. It is vitally important (for clear reasons) that the implant be biologically stable and not cause irritation or another undesirable reaction while in the body. Furthermore, consideration should be given to an implant's potential effect on diagnostic, imaging, monitoring and other therapeutic technologies necessary to care for post-operative patient care.

The speed and ease of installation are important considerations to make when choosing an implant fixation construct. Cardiovascular surgeons are not orthopedists and therefore not routinely familiar with drills, screwdrivers and other "bone carpentry" tools. Many sternum closure devices currently offered require such items as they are based on orthopedic plate and screw technology. These devices typically require multiple instruments, have many individual parts, and take an excessive amount of time to install adding additional time and cost to the surgery.

The speed and ease of implant removal are also critical factors when choosing a fixation implant construct, especially in the case of a target sternum whereby emergency surgical re-access may be required should the patient incur a life-threatening health event necessitating surgical reentry of the chest wall. If a device requires special instruments to remove or has become biologically imbedded in the soft tissues and/or bone, valuable time can be lost dealing with locating removal instrumentation and exposing and removing the implants.

Additionally, the cost of an implant device construct must be reasonable and not add significantly to the overall cost of performing surgery. In the case of the sternum cerclage wire fixation, the material cost of surgical wire is insignificant. Plate and screw constructs for sternal closure range in price but can be costly per device. In addition, there are disposable components, such as drill bits, etc., that add to the cost and complexity of surgery. All known sternum-plating sets are configured as reusable trays containing an assortment of implants and reusable instruments requiring sterilization, cleaning, and restocking and storage between each use requiring additional costs and labor.

Typical sternal fixation devices include rigid-plate constructs with elaborate locking screws whereby the screws simultaneously thread into the plate and sternum which prevents the screws from becoming detached from the plate in the event they strip and become dislodged from the sternal bone. The instructions for use of such systems (such as available from Synthes and Biomet Microfixation) typically recommend a minimum of three plates and the placement of multiple screws to affix each plate to each independent bone segment. The plates are spaced and implanted along the anterior facing sternal surface midline straddling the saw cut with screws inserted into the sternum on both sides of the cut. Synthes offers a plate configuration that comprises of two halves joined together in the center with a removable u-shaped pin. If emergency re-access becomes necessary, the operator may remove the pins and separate the sternum and associated rib attachments left and right giving immediate access through the chest wall. However, uncoupling the plate assembly only immobilizes the underlying bone while the bone remains unhealed. If reentry is attempted after the soft tissue and/or bones have partially or fully united, simply removing the pins will not allow immediate re-access. In such instances, the bulky metal plates would interfere with a saw cut being made through the sternum in the conventional way without first removing the plates and screws, adding time and placing the patient at additional risk if access through the chest wall is urgently needed. Such screw-secured implants are also very time-consuming to implant and costly. Furthermore, their excessively rigid construction can result in stress shielding leading to poor bone quality and strength or delayed healing. Biomet Microfixation attempts to overcome the limitation of the Synthes design by making their plates cuttable in the center; however, a special cutting instrument is still required to cut and remove sections of implanted plates.

In another variation of a prior device, reduced stress shielding has been provided through the utilization of braided cables through sterna-positioned cannulated metallic grommets. Unfortunately, though, this alternative still requires excessive operating time and a skill-dependent implantation procedure. The cable is laced along the sternum like laces on a shoe and tightened with a special cable crimping instrument. The process for installation is too cumbersome and time consuming and getting the bone segments back into anatomical position has proven too difficult for widespread, reliable use.

Self-locking fasteners, such as or similar to cable ties or zip ties placed circumferentially around the sternum through the intercostal spaces provide improved simplicity and potential time savings compared to wire fixation, but do not provide enough stability to adequately immobilize the bone segments sufficiently to achieve desirable and reliable healing for all patients. Like wire fixation, the zip tie fixation method disregards the significant forces loading on the sternum and is not an adequate solution for, in particular, at risk patients. Therefore, it appears to be a potentially more convenient way to achieve the same benefits of cerclage wiring.

Another available device designed for closing the chest wall and holding the sternum together following median sternotomy consists of a mechanical clamp that cleats around the sternum passing through the intercostal spaces. When used in series, these metallic clamps sold by KLS Martin compress the sternum together. The clamps are large, excessively rigid and frequently uncomfortable and irritating to the patient frequently necessitating post-operative removal, as well as comparatively costly. They also interfere with common imaging technologies including x-ray, CT and MRI.

There is a device available from Acute Innovations called Acutie that supposedly enhances the strength and stability of a cerclage wire construct. Surgical wire is passed around the sternum through the intercostal spaces and inserted through slots in a stainless steel plate, then tensioned and crimped. The method calls for multiple plates spaced along the anterior aspect of the sternum. The plates are substantially stronger than the bone and only prevent wire abrasion on a limited surface area of the sternum thus would seem to provide little benefit over wire fixation alone. The potential for wire to loosen, break and/or cut through bone is not entirely eliminated and might even be enhanced due to the plate stiffness transferring more load to the wire section in direct contact with bone.

Other identified competitive offerings tend to follow a plate and screw approach to fixing the sternum, typically with cuttable struts across the central section facilitating removal. None of them appear to offer significant benefits over each other and due to the significant forces that act on the sternum under extreme functional loading all present similar risks of complication due to inadequate load distribution and dissipation.

What is needed, then are improvements in devices and methods for securing and fixating the sternum following fracture or surgery.

BRIEF SUMMARY

The present disclosure provides devices and associated methods for sternum fixation following fracture or surgery. Such devices and methods provide for fixation of a fractured or surgically cut sternum bone using a plate and a plurality of fastener bands engaging the plate and configured to secure the plate to the sternum bone by passing around the bone and back into the plate.

In some aspects of the disclosure, a sternum fixation device includes a plate having a first end and a second end, a right lateral edge and a left lateral edge, an inner side configured for placement against the sternum, and an outer side configured to face away from the sternum. A first lobe is disposed at the first end of the plate. The first lobe includes a band socket defined as a blind recess in the outer side of the plate. The band socket includes a right lateral stop and a left lateral stop opposite the right lateral stop. A right lateral channel is defined in the first lobe from the right lateral edge to the band socket. The right lateral channel is defined above a right side floor in the socket. A left lateral channel opposite the right lateral channel is defined in the first lobe from the left lateral edge to the band socket. The left lateral channel is defined above a left floor in the socket. The left lateral stop protrudes from the left lateral channel inwardly into the socket at an inclined angle above the left floor of the socket forming a wedge-shaped recess in the socket. The right lateral stop comprises first and second tapered walls extending upwardly from the right floor in the socket toward the right lateral channel.

Another feature of the present disclosure provides a sternum fixation plate including a socket that receives a similarly shaped head of a fastener band therein. The socket includes right and left lateral stops to prevent the band from moving laterally when the band is being inserted around the sternum and tightened.

A second aspect of the present disclosure provides a method for sternum fixation. The method includes the steps of (a) providing a plate including a plurality of lobes, each lobe having a band socket shaped to receive a corresponding band with a head and a strap; (b) inserting the head into the band socket; (c) passing the strap around the sternum and back through the head on an opposite lateral side of the plate; (d) inserting the strap into an aperture on a handheld tensioning and cutting device; and (e) actuating a tensioning lever on the tensioning and cutting device to pull the strap to a pre-determined tension and to also cut the strap once the pre-determined tension is achieved.

The method further includes performing steps (b) through (e) for additional bands on the same plate until the plate is fully secured to the sternum.

The advantages discussed herein may be found in one, or some, and perhaps not all of the aspects disclosed herein. Additional features and advantages are described herein, and will be apparent from, the following Detailed Description and the Figures.

BRIEF DESCRIPTION OF THE DRAWINGS

The accompanying drawings, which are incorporated herein and constitute part of this specification, illustrate certain preferred aspects of the invention, and, together with the general description given above and the detailed description given below, serve to explain the features of the invention.

FIG. 13 is an inner side perspective view of an embodiment of a fastener band for use with a sternum fixation device in accordance with the present disclosure.

FIG. 14 is an outer side view of an embodiment of a fastener band for use with a sternum fixation device in accordance with the present disclosure.

DETAILED DESCRIPTION

While the invention is described in connection with certain preferred aspects, it is not intended that the present invention be so limited. On the contrary, it is intended to cover all alternatives, modifications, and equivalent arrangements as may be included within the spirit and scope of the invention as defined by the appended claims.

The drawings provide illustrative, non-limiting aspects of the present invention setting forth an exemplary packaging and display apparatus and associated methods. Certain terminology is used herein for convenience only and is not to be taken as a limitation on the present invention. While the following describes certain illustrative aspects of the present invention, it should be understood, based on this disclosure that the invention is described by the claims, and is not limited by the aspects described herein.

The present disclosure provides devices and methods for sternum fixation. The device of the present disclosure generally includes an elongated plate comprising a plurality of sockets shaped to receive one or more fasteners. Each fastener includes a strap or band that extends from the plate, around the sternum bone, and back to the plate. Each fastener may be secured and tightened to hold the plate against the sternum bone and also to hold the two sternum halves, or sections, in place to promote healing.

Figure 1:
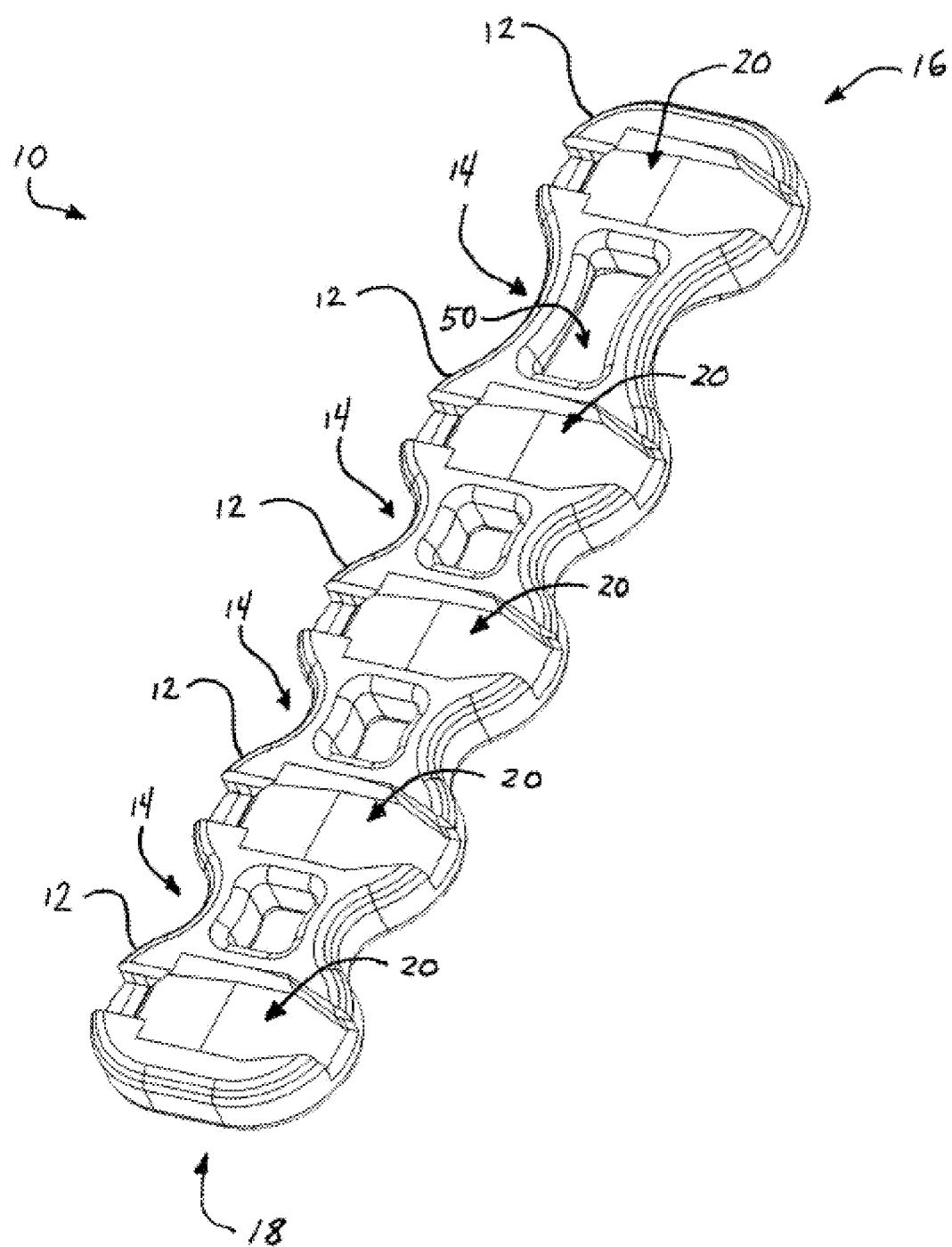
FIG. 1 is a front side perspective view of a sternum fixation device in accordance with the present disclosure.

Referring to FIG. 1, an embodiment of a sternum fixation device is illustrated. The device includes an implant construct for stabilizing and healing fractured or surgically cut bone. The implant includes a plate 10 having a longitudinal shape with a first end 16 and a second end 18. In some embodiments, first end 16 is configured to be positioned against the upper sternum in the region of the manubrium oriented toward the jugular notch, and the second end 18 is configured to be positioned against the lower sternum oriented toward the xiphoid process. Plate 10 also includes a right lateral edge shown on the right side of the device of FIG. 1, and a left lateral edge shown on the left side of the device of FIG. 1.

Plate 10 includes a plurality of lobes 12 connected by interspaced bridges 14. Each lobe includes a wider portion of plate 10 as compared to the adjacent bridges 14 in some embodiments, which included necked or recessed widths. Each lobe is configured to be aligned generally with an intercostal space of the rib cage to allow travel of a corresponding fastener band through the intercostal space and around the sternum. In some embodiments, as shown in FIG. 1, plate 10 includes five lobes 12 spaced along the length of the plate 10. In other embodiments, plate 10 may include more than five, or fewer than five lobes.

Referring further to FIG. 1, plate 10 includes a plurality of band sockets 20. Each band socket is configured to receive a corresponding portion of a band. Each band socket 20 includes a recess defined in the outer surface of the plate 10, on the side of the plate 10 facing away from the patient's body. Each band socket 20 forms a blind recess having a bottom surface comprising the plate material. Each band socket 20 may be integrally formed in plate 10 during a molding or manufacturing process, or may be machined in the surface of plate 10 following molding, casting or machining of the plate 10.

In some embodiments, as shown in FIG. 1, each lobe 12 has a corresponding band socket 20 defined thereon. As such, each lobe 12 may be securely pressed against the sternum when its corresponding band is installed in its band socket 20, and when the band is tightened. Each band extends from its corresponding band socket 20 in a lateral direction generally perpendicular to the longitudinal axis of plate 10, circumscribing a loop around the sternum, and returning back to the plate 10 on the opposite lateral edge.

Also shown in FIG. 1, a plurality of holes 50 are defined through plate 10 from the outer side to the inner side. Each hole 50 provides an opening for passage of wire, sutures, tissue or other materials if needed during or after an operation. Additionally, each hole provides a passage for fluid or other body materials to drain or pass. In some embodiments, each hole 50 is defined as a clearance passage through a corresponding bridge 14. As such, each hole 50 is positioned between corresponding band sockets 20 on bridges 14. Thus, each hole 50 and each band socket 20 are axially spaced from each other along a longitudinal axis of plate 10 extending from first end 16 to second end 18.

Figure 2:
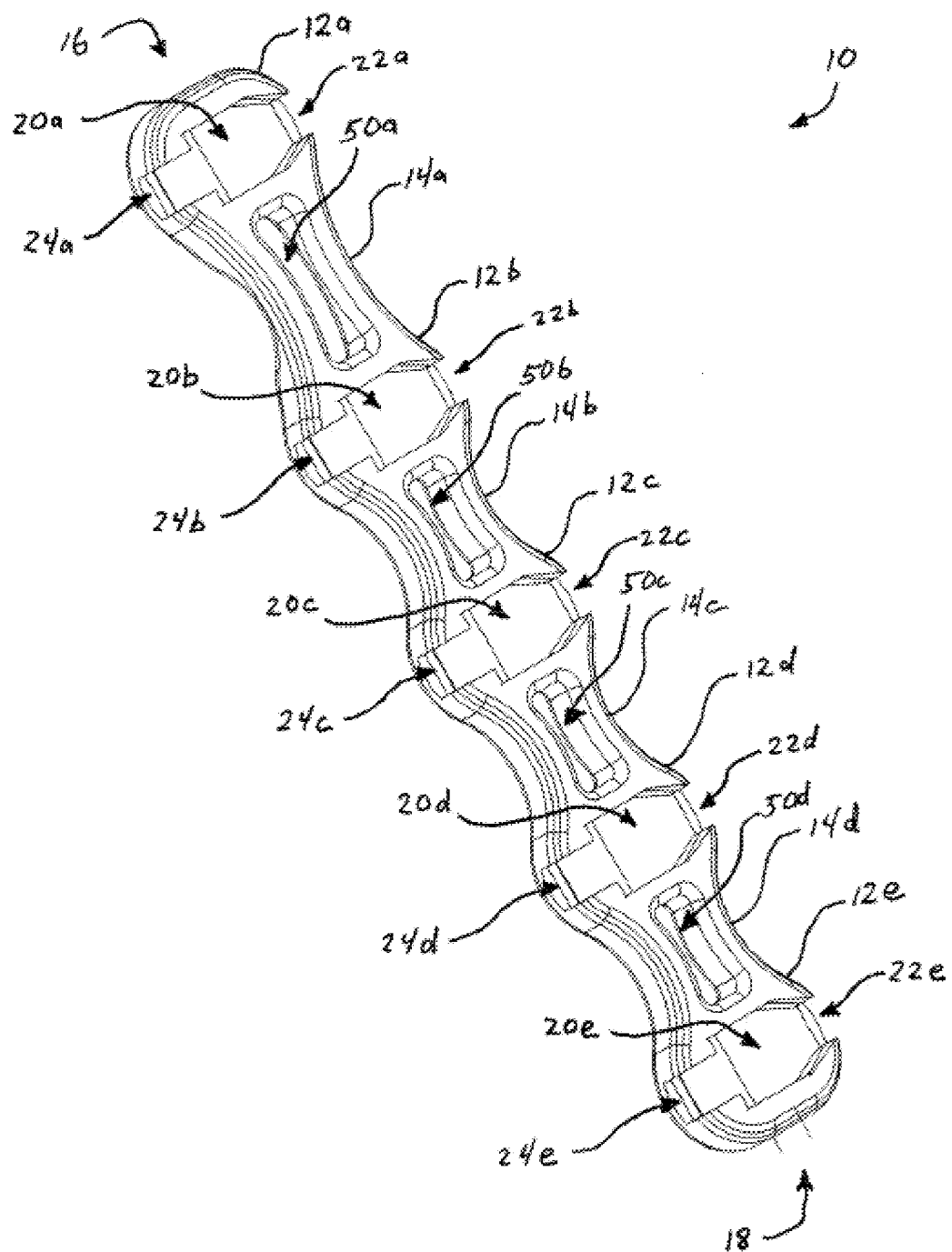
FIG. 2 is a front side perspective view of a sternum fixation device in accordance with the present disclosure.

Referring now to FIG. 2, an embodiment of a surgical implant for sternum fixation including a plate 10 is shown in a left lateral side perspective view. Plate 10 includes a first lobe 12a including a first band socket 20a. First lobe 12a is attached to second lobe 12b by first bridge 14a. First bridge 14a includes a first hole 50a defined therein in some embodiments. First hole 50a is a clearance hole defined entirely through plate 10 from the outer side to the inner side.

Second lobe 12b is positioned between first lobe 12a and third lobe 12c. Second lobe 12b includes a second band socket 20b defined in second lobe 12b. Second lobe 12b is attached to third lobe 12c by second bridge 14b. Second bridge 14b includes a second hole 50b defined therein in some embodiments. Second hole 50b is a clearance hole defined entirely through plate 10 from the outer side to the inner side. In some embodiments, second hole 50b has a different shape than first hole 50a to accommodate different shapes of the sternum at the respective locations of the first and second holes 50a, 50b.

Third lobe 12c is positioned between second lobe 12b and fourth lobe 12d. Third lobe 12c includes a third band socket 20c defined in third lobe 12c. Third lobe 12c is attached to fourth lobe 12d by third bridge 14c. Third bridge 14c includes a third hole 50c defined therein in some embodiments. Third hole 50c is a clearance hole defined entirely through plate 10 from the outer side to the inner side. In some embodiments, third hole 50c has a different shape than first hole 50a to accommodate different shapes of the sternum at the respective locations of the first and third holes 50a, 50c. In some embodiments, third hole 50c and second hole 50b have substantially the same shape.

Fourth lobe 12d is positioned between third lobe 12c and fifth lobe 12e. Fourth lobe 12d includes a fourth band socket 20d defined in fourth lobe 12d. Fourth lobe 12d is attached to fifth lobe 12e by fourth bridge 14d. Fourth bridge 14d includes a fourth hole 50d defined therein in some embodiments. Fourth hole 50d is a clearance hole defined entirely through plate 10 from the outer side to the inner side. In some embodiments, fourth hole 50d has a different shape than first hole 50a to accommodate different shapes of the sternum at the respective locations of the first and fourth holes 50a, 50d. In some embodiments, fourth hole 50d, third hole 50c and second hole 50b all have substantially the same shape.

Fifth lobe 12e is positioned below fourth lobe 12e on the second end 18 of plate 10. Fifth lobe 12e includes a fifth band socket 20e defined in fifth lobe 12e. Fifth lobe 12e is attached to fourth lobe 12d by fourth bridge 14d on one side. Fifth lobe 12e is the lowest lobe on plate 10 in some embodiments, and is configured to be oriented toward the xiphoid process on the sternum.

Referring further to FIG. 2, each band socket 20a, 20b, 20c, 20d, 20e is defined as a blind recess in its corresponding lobe. First band socket 20a is oriented such that its corresponding band will extend from and return to plate 10 in a lateral direction substantially perpendicular to the longitudinal axis of plate 10. First band socket 20a includes a right lateral channel 22a on a right lateral edge of first lobe 12a on plate 10. Right lateral channel 22a is a blind U-shaped recess defined in the right lateral edge of first lobe 12a. Right lateral channel 22a is shaped to allow passage of a fastener band extending from first band socket 20 away from plate 10.

First band socket 20a also includes a left lateral channel 24a on a left lateral edge of first lobe 12a on plate 10. Left lateral channel 24a is shaped to allow passage of the fastener band. Right and left lateral channels 22a, 24a are defined on opposite lateral edges of first lobe 12a on the outer side of plate 10. Each of right and left lateral channels 22a, 24a have a bottom such that the fastener band exits and enters first band socket 20a along the outer surface of plate 10 and presses down against the plate 10 when tightened. As such, the band enters and exits the plate 10 from the lateral edges above the floor (i.e. on the side opposite the sternum), not from openings on the underside of the plate 10 adjacent to the sternum.

Similar second, third, fourth and fifth band sockets 20b, 20c, 20d, 20e include corresponding right lateral channels 22b, 22c, 22d, 22e and left lateral channels 24b, 24c, 24d, 24e on second, third, fourth and fifth band sockets 12b, 12c, 12d, 12e, respectively. Each band socket includes the same features discussed herein with respect to first band socket 20a in some embodiments.

Figure 3:
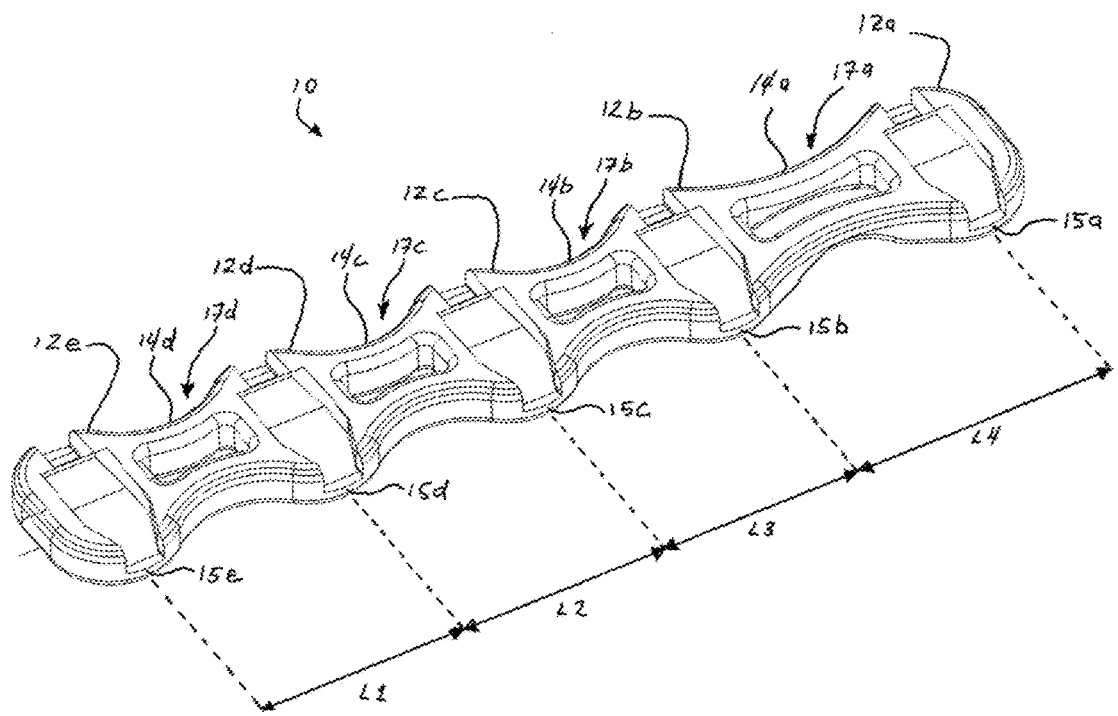
FIG. 3 is a front side perspective view of a sternum fixation device in accordance with the present disclosure.

Referring to FIG. 3, an embodiment of a surgical implant for sternum fixation including a plate 10 is shown in a right lateral side perspective view. In some embodiments, plate 10 is shaped to be aligned with the physical structure of the sternum. For example, first, second, third fourth and fifth lobes 12a, 12b, 12c, 12d, 12e each includes a lateral apex 15a, 15b, 15c, 15d, 15e. The spacing between each adjacent lateral apex may be dimensioned carefully to size the plate 10 to a desired sternum size or shape. In some embodiments, first lobe 12a and second lobe 12b are separated by an axial distance L4, second lobe 12b and third lobe 12c are separated by an axial distance L3, third lobe 12c and fourth lobe 12d are separated by an axial distance L2, and fourth lobe 12d and fifth lobe 12e are separated by an axial distance L1. In some embodiments, L1, L2 and L3 are substantially equal, and L4 is greater than L1, L2 and L3. The dimensions L1, L2, L3 and L4 are customized to accommodate intercostal spacing between a patient's ribs. In some embodiments, L4 is larger than the other dimensions to accommodate flexure of first lobe 12a at first bridge 14a inwardly toward the manubrium.

Referring further to FIG. 3, each bridge 14a, 14b, 14c, 14d includes a narrower lateral width than the adjacent lobes 12a, 12b, 12c, 12d, 12e. As such, a corresponding lateral notch 17a, 17b, 17c, 17d, 17e is formed on each lateral side of plate 10 between lobes.

Figure 4:
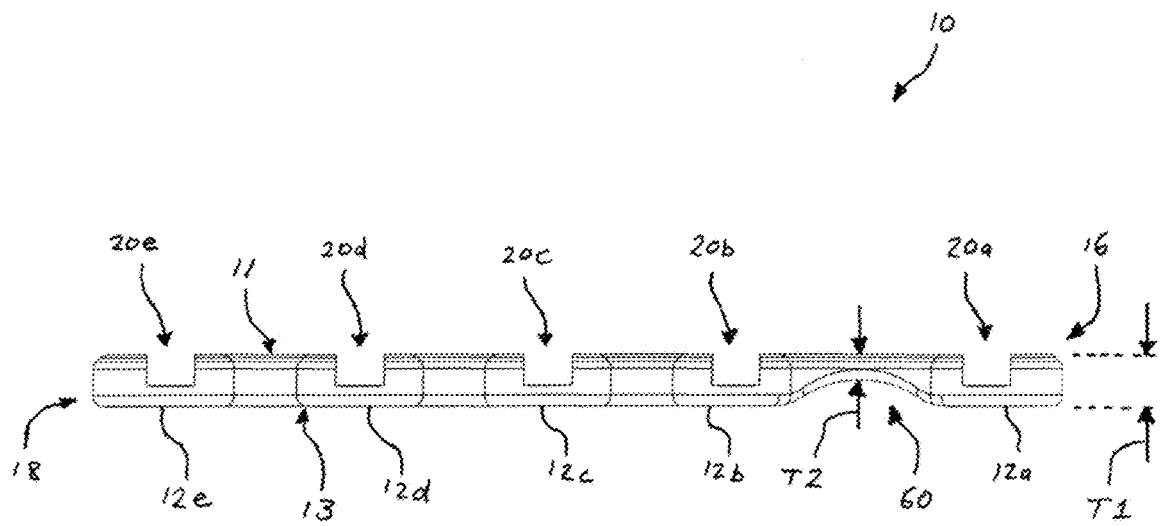
FIG. 4 is a lateral side view of a sternum fixation device in accordance with the present disclosure.

Referring to FIG. 4, a side lateral view of a surgical implant for sternum fixation including a plate 10 is shown. Plate 10 includes a first end 16 and a second end 18 at opposite longitudinal ends. Plate 10 also includes an outer side 11 and an inner side 13. Outer side 11 is configured to face away from the patient's body when the plate 10 is implanted. Inner side 13 is configured to face toward the patient's body and contact the patient's sternum when the plate 10 is implanted.

As shown in FIG. 4, inner side 13 is substantially flat along the length of the plate 10, and plate 10 includes a substantially uniform major thickness T1 along its length, except for an arcuate recess 60 defined in plate 10 between first lobe 12a and second lobe 12b. Recess 60 forms a minor thickness T2 on first bridge 14a. T2 is less than T1 in some embodiments. Recess 60 forms a living hinge in plate 10 allowing first lobe 12a to bend or flex toward the sternum to accommodate the sternal angle near the manubrium. In some embodiments, the ratio of T1/T2 is between about 1.0 and about 3.0. In further embodiments, the ratio of T1/T2 is between about 1.0 and about 2.0.

Figure 5:
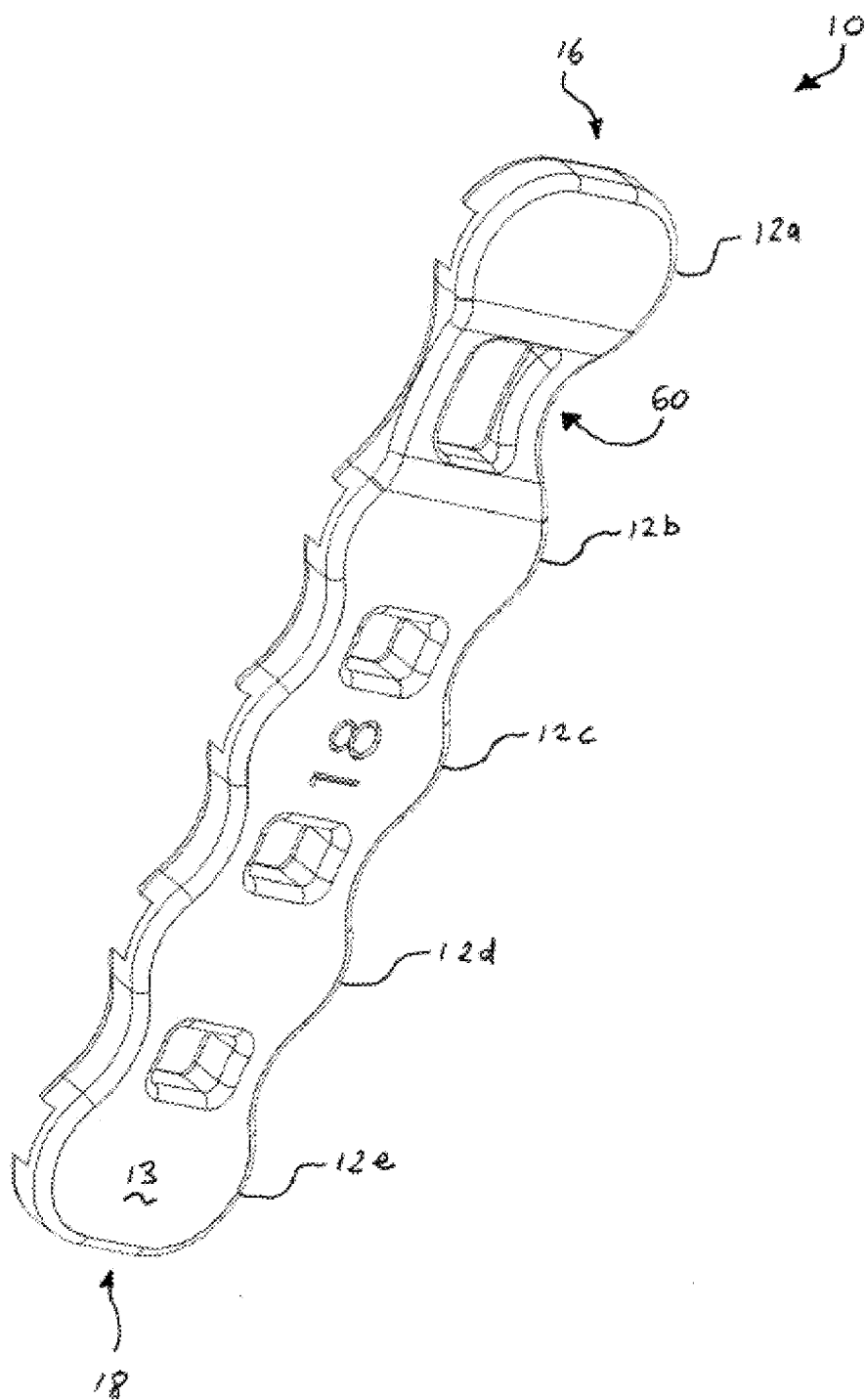
FIG. 5 is a back side perspective view of a sternum fixation device in accordance with the present disclosure.

Referring to FIG. 5, a back perspective view of a surgical implant for sternum fixation including a plate 10 is shown. The inner side 13 of plate 10 is configured to be placed against a patient's sternum. In some embodiments, inner side 13 is substantially flat, with arcuate recess 60 defined between first lobe 12a and second lobe 12b.

Figure 6:
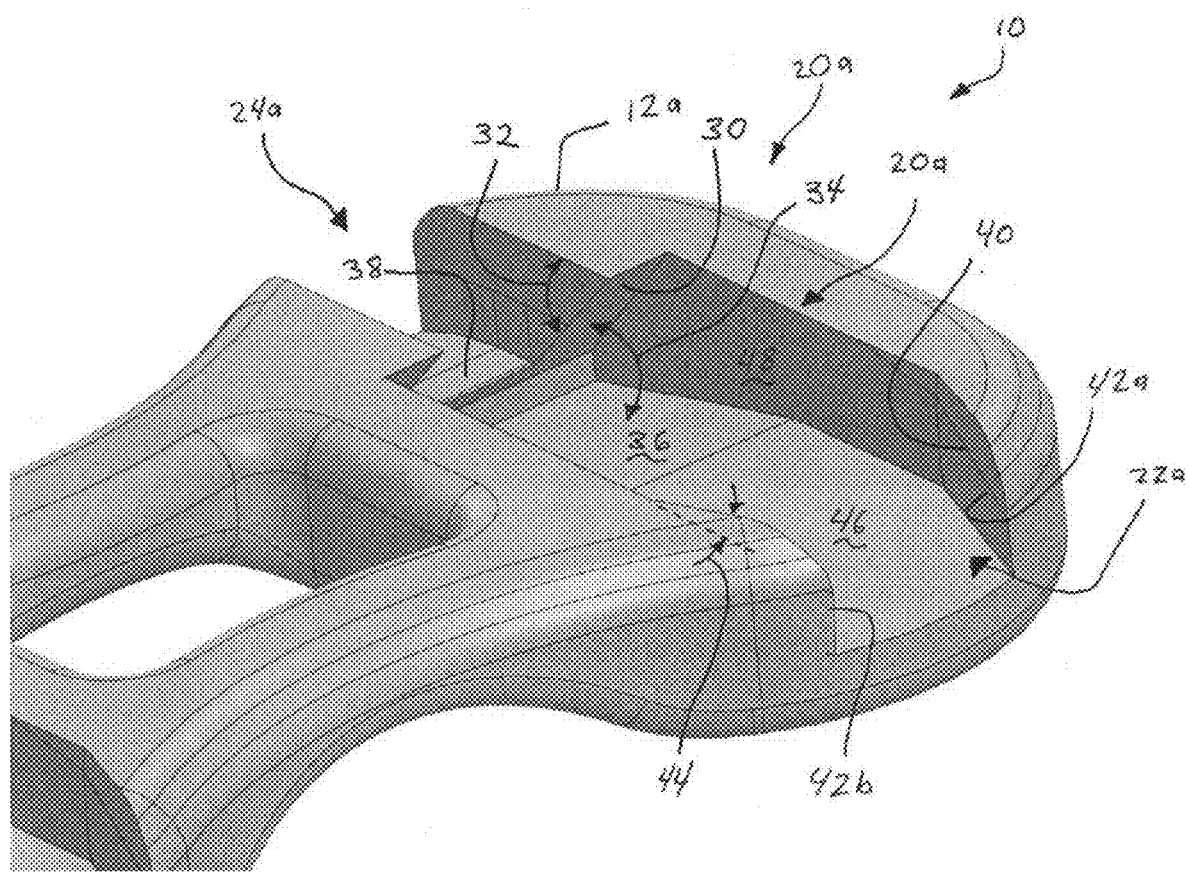
FIG. 6 is a detail right lateral side perspective view of a sternum fixation device in accordance with the present disclosure.
Figure 7:
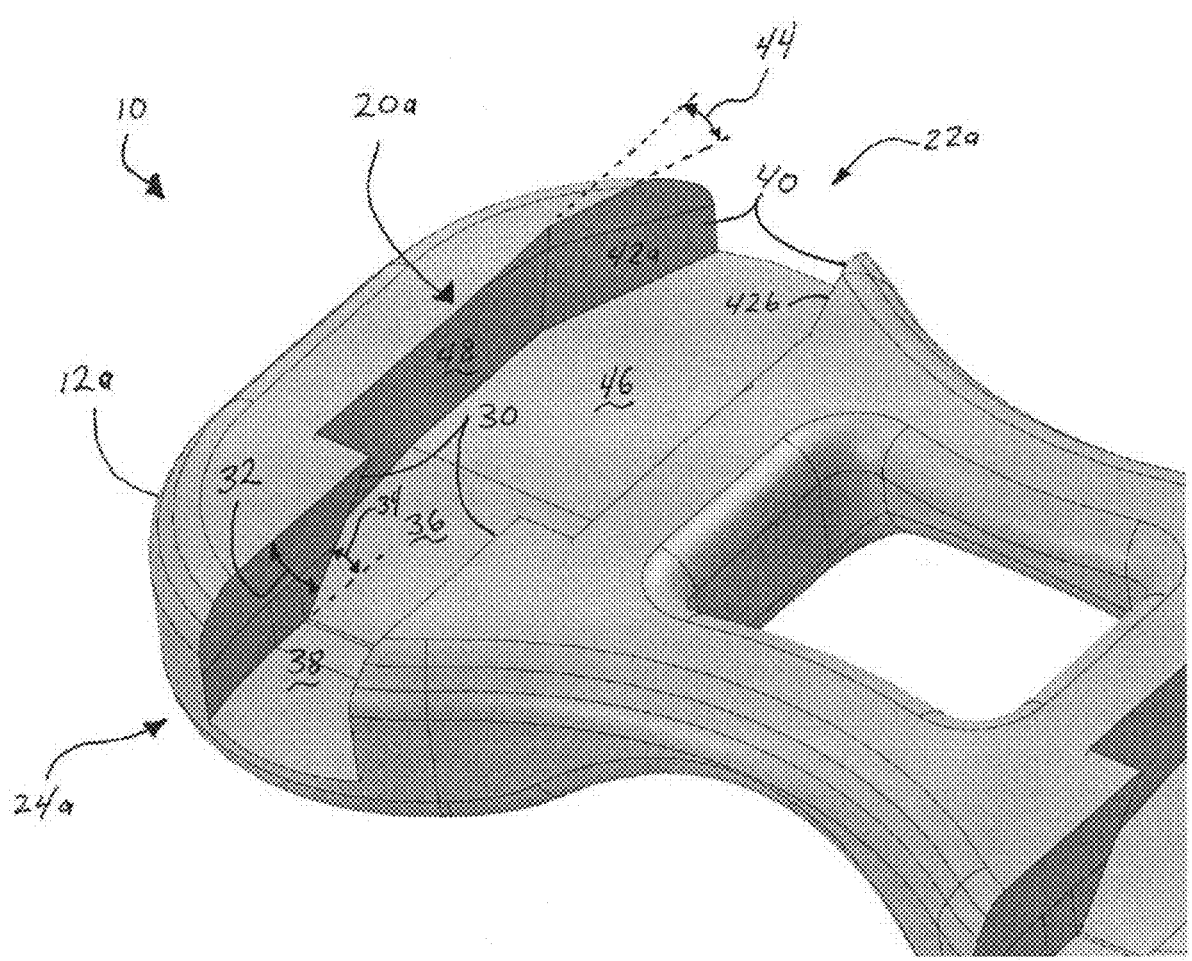
FIG. 7 is a detail left lateral side perspective view of a sternum fixation device in accordance with the present disclosure.
Figure 8:
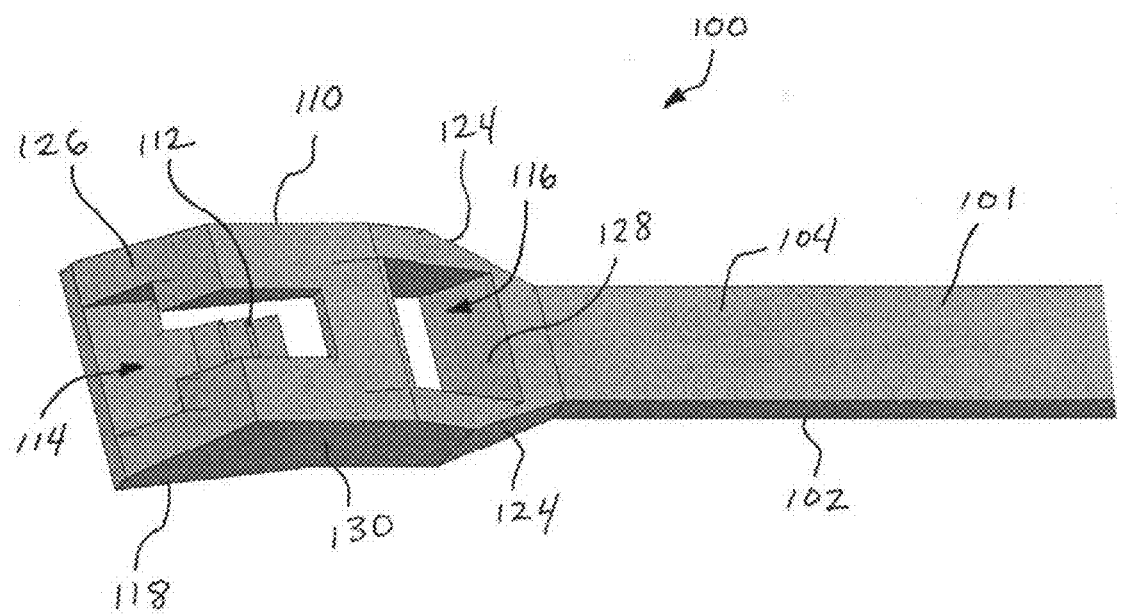
FIG. 8 is a top perspective view of an embodiment of a fastener band for use with a sternum fixation device in accordance with the present disclosure.
Figure 9:
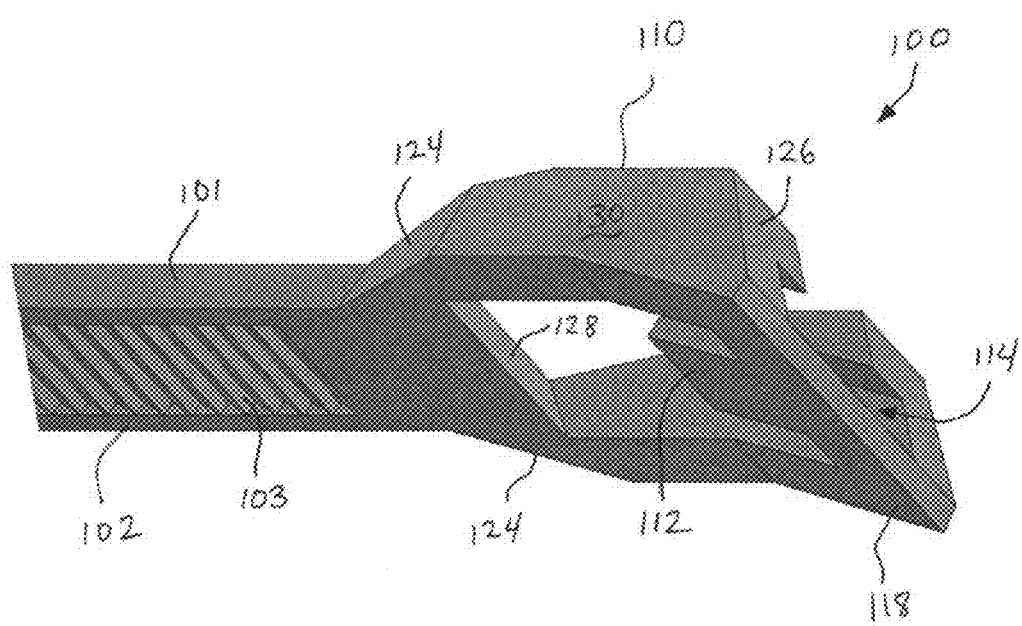
FIG. 9 is a bottom perspective view of an embodiment of a fastener band for use with a sternum fixation device in accordance with the present disclosure.
Figure 10:
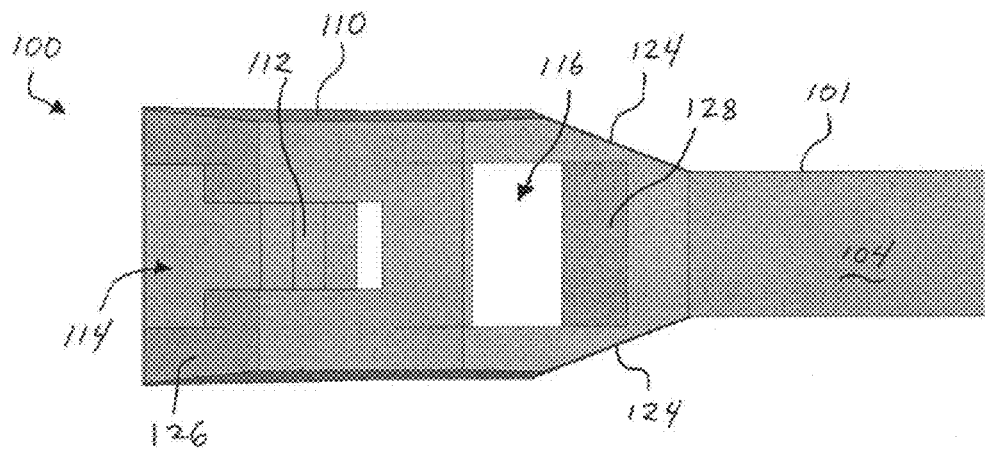
FIG. 10 is a top view of an embodiment of a fastener band for use with a sternum fixation device in accordance with the present disclosure.
Figure 11:
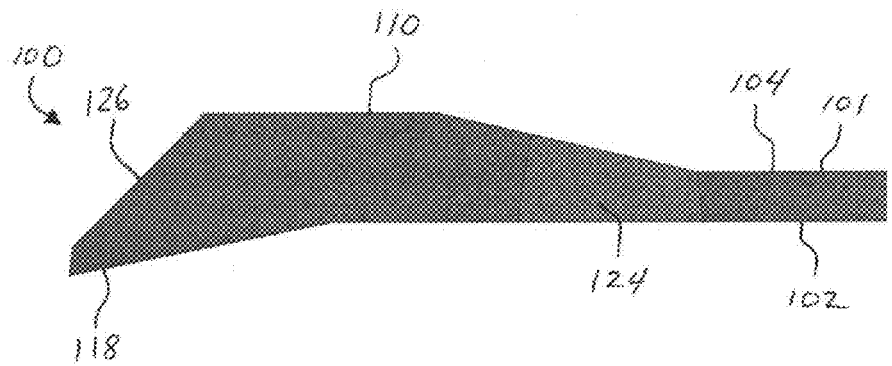
FIG. 11 is a side view of an embodiment of a fastener band for use with a sternum fixation device in accordance with the present disclosure.

Referring to FIG. 6 and FIG. 7, detail perspective views of embodiments of the right lateral and left lateral sides of a plate 10 are shown. Plate 10 includes a first band socket 20a defined in the outer side of the plate. First band socket 20a is configured to receive a portion of a fastener band for securing plate 10 to a sternum. First band socket 20a includes a blind recess defined in the plate, with the recess shaped to receive a corresponding head of a band in a press fit or a snap fit engagement. The head of a corresponding band may be inserted downwardly into the recess formed by the first band socket 20a.

First band socket 20a includes numerous technical features configured to optimize engagement with a band, and particularly with the head of a band, for fast, safe and efficient installation and tightening of the band.

As shown in FIG. 6, in some embodiments, first band socket 20a includes a left lateral stop 30 on the left lateral side of the socket, and a right lateral stop 40 on the opposite right lateral side of the socket. Left lateral top 30 protrudes medially into the socket from the left lateral side at an inclined angle 32. Left lateral stop 30 extends along a plane substantially parallel to the longitudinal axis of the plate 10 such that a band head will transversely press against the left lateral stop 30, thereby limiting lateral travel of the band head in the direction of the left lateral stop 30.

A left floor 36 is defined at the bottom surface of first socket 20a adjacent left lateral stop 30. Left floor 36 is inclined, sloping downwardly toward left lateral stop 30. An angle 36 is defined between left lateral stop 30 and left floor 36. Floor angle 34 is less than inclined angle 32 in some embodiments. A step 38 is formed at the intersection of left lateral stop 30 and left lateral channel 24a. Step 38 drops off into the wedge-shaped recess formed by left floor 36 and left lateral stop 30.

Similarly, a right lateral stop 40 includes tapered side walls 42a, 42b constricting the dimension of the socket laterally toward right channel 22a. First and second tapered walls 42a, 42b are each inclined at a right lateral stop angle 44. Right lateral stop angle 44 on each tapered side wall 42a, 42b is between about five degrees and about sixty degrees in some embodiments.

A right floor 46 is defined at the bottom surface of first socket 20a adjacent right lateral stop 40. Right floor 46 is substantially flat and defined in a plane parallel to the major plane of plate 10. Right floor 46 provides a surface against which a fastener band may rest when tightened on plate 10.

Referring to FIG. 8 to FIG. 11, an embodiment of a fastener band 100 is shown. Band 100 includes a strap 101 and a head 110. Strap 101 and head 110 are integrally molded together as a one-piece construct in some embodiments. Strap 101 includes an inner side 102 configured to be placed face-down against the plate 10 and patient tissue, and an outer side 104 configured to face away from the plate 10 and patient tissue. Inner side 102 includes a plurality of transverse ridges, barbs or detents 103 shaped to engage corresponding structure on head 110 in a locking engagement.

Head 110 is shaped to closely match the contours of a band socket 20 on plate 10, such that head 110 and band socket 20 each have an interlocking geometry. Head 110 and band socket 20 are keyed to facilitate proper alignment and engagement. Head 110 includes an end wall 126 shaped to engage first stop 30. End wall 126 forms a wedge-shaped protrusion 118 that fits closely in the angled gap formed by left lateral stop 30 and left floor 36. A head entry opening 114 is defined in end wall 126 shaped to receive a free end of strap 101 passing into head 110 through lateral channel 24a. An anti-reverse latch 112 inside head 110 provides a locking engagement with the inner side 102 of strap 101 when strap 101 is inserted into entry opening 114. An exit opening 116 is defined in head 110 to allow the free end of strap 101 to pass out of head 110 after engaging latch 112. The free end passing out of exit opening 116 slides up along ramp 128 and may be trimmed flush to head 110 once tightened. After trimming, the tag end of strap 101 is retained in a low profile in the head 110 to prevent snagging on tissue or irritation to the patient.

Referring further to FIG. 8 to FIG. 11, head 110 includes a shoulder 124 keyed to facilitate proper engagement with right lateral stop 40 on plate 10. Shoulder 124 on band 100 includes a tapered profile inclined to match the angle of each right lateral stop wall 42a, 42b alongside right channel 22a. The engagement between shoulder 124 and walls 42a, 42b prevents head from sliding out of the socket 20 when the band is tightened. Thanks to the specific interlocking geometry provided between head 110 and socket 20, head 110 matches the profile of socket 20 to retain head 110 securely in socket 20a when band 100 is being passed around behind the sternum, back into the plate on the opposite lateral edge, tightened and trimmed.

Figure 12:
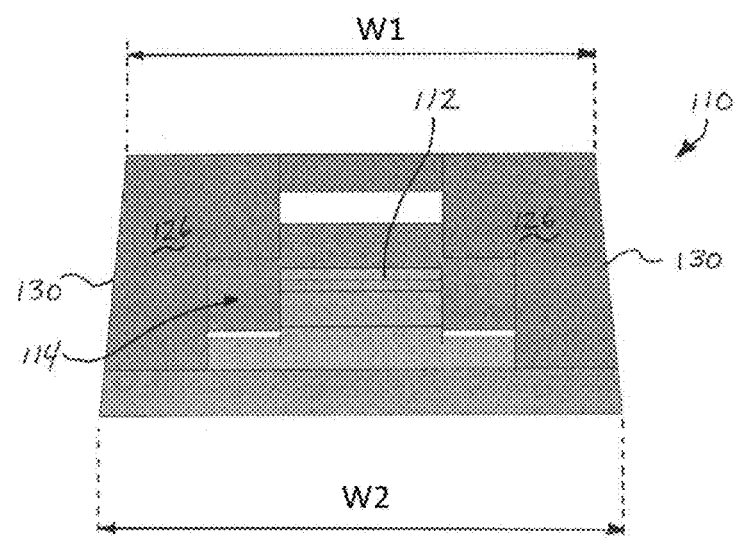
FIG. 12 is an end view of an embodiment of a fastener band for use with a sternum fixation device in accordance with the present disclosure.

Referring to FIG. 12, an embodiment of head 110 includes a trapezoidal profile in some embodiments. For example, head 110 includes a top width W1 less than a bottom width W2. As such, side walls 130 are slightly tapered inwardly. Such a configuration helps secure head 110 in socket 20, as the tapered walls 130 prevent head 110 from sliding upwardly and lifting out of socket 20 during tightening or during healing.

As shown in FIG. 13 and FIG. 14, examples of fastener bands 100 are shown. Each band includes a head 110 and a strap portion 101. Band 100 includes a pre-formed curved section 120 with a tip 122 configured for insertion into and through tissue around the sternum for passing the strap 101 behind the sternum and back into the entry opening 114 for engagement with the locking member 112 on head 110.

In some embodiments, plate 10 is flexible and is configured to conform to the shape of the sternum bone. The plate is configured such that the loads applied to the plate correspond to intercostal spaces between ribs. By using a unibody structure for plate 10 that runs the length of the bone or surgical cut and conforms to an irregular shape by activation of tension under compressive force of the bands, certain biomechanical advantages may be achieved over other conventional devices and methods which rely on multiple plates or other structures.

Method of Securing Sternum

In some additional embodiments, the present disclosure provides a bone repair device and instrumentation, and associated methods. An implant construct and application instrument for stabilizing and healing fractured and surgically cut bone. The implantable components consist of a plate and a series of attachable fasteners that may dock to the plate upon assembly. The plate is placed on the surface of a fractured or surgically cut bone generally in plane with its long axis. A series of fasteners that may attach to or pass freely over the plate body and the underlying bone are generally oriented perpendicular in relationship to the long axis of the injured bone and plate body circumscribing the contour forming loops. The fasteners may attach to plate body by a variety of means and/or attach to themselves when the opposing fastener ends are joined by means of a buckle consisting of male and female ends. Tensioning of the fastener loops simultaneously compresses the plate and bone components together forming a splint providing adequate stability for healing. The plate provides sufficient stiffness and rigidity to buttress the injured bone while providing sufficient ductility to conform to the shape and contours of the underlying bone upon the tensioning of the corresponding fasteners.

Precise fastener tensioning and cutting is performed with a special instrument that, in some embodiments, resembles a handgun in general shape. The instrument consists of a hand grip, actuating trigger/lever, body and barrel. The barrel contains a channel/chamber along its length. The free end of a fastener to be tensioned is inserted into the channel through its aperture at the end of the instrument barrel. The aperture of the channel corresponds to the shape of the fastener so that the free end of a fastener precisely feeds through the channel in a controlled manner. Upon continuous actuation of the lever, the fastener is advanced through the channel which, in turn, tensions the fastener by activating a buckling action as the result of a fastener threading through a locking mechanism either imbedded in a plate or contained within the opposing end of the same fastener. The buckling action permits ingress of a fastener as it passes through a cavity containing a locking mechanism while preventing egress in the opposing direction.

In some embodiments, the instrument contains a clutch mechanism that limits the amount of tension that can be applied to a fastener. When a prescribed level of tension is generated, the instrument disengages preventing further tensioning or over-tensioning of a fastener. This feature prevents user error and avoids relying on user judgment based on prior experience, visualization or tactile feel. The instrument can be removed at any time and only grips upon a fastener when the lever is being actuated.

The instrument can be subsequently reintroduced over the exposed free end of a fastener should additional tensioning be necessary. It also contains a cutting mechanism and blade to trim/cut and remove the redundant residual free end of a fastener after tensioning has been performed. The cutting feature is located at the tip of the instrument barrel end and may be actuated with the same lever used for tensioning. Placement of the cutting feature at the tip of the instrument ensures a flush cut so no portion of the remaining fastener protrudes though a locking mechanism which could irritate overlying tissues and/or be palpated by the patient and potentially cause discomfort.

A safety switch prevents premature or unintended fastener cutting until the operator has determined the appropriate timing to complete the task. Alternatively, a secondary lever is added to the instrument to actuate cutting in some embodiments. The precise feeding of a fastener through the instrument channel maintains a perpendicular relationship between fastener and cutting blade to ensure a clean and straight cut with no jagged edges. Furthermore, a spring loaded probe located at the tip of the instrument barrel may be added, the purpose of which is to require depressing the probe into a corresponding barrel cavity in order activate the cutting function. This would prevent premature or unintentional fastener cutting and only allowing cutting when the instrument tip and cutting blade are seated at the lowest and most optimal position to ensure a flush cut with the free end of a fastener concurrently passing through the instrument channel. Free ends of fasteners that have been cut can be easily removed from the instrument upon deactivation or release of the tensioning lever.

Figure 15:
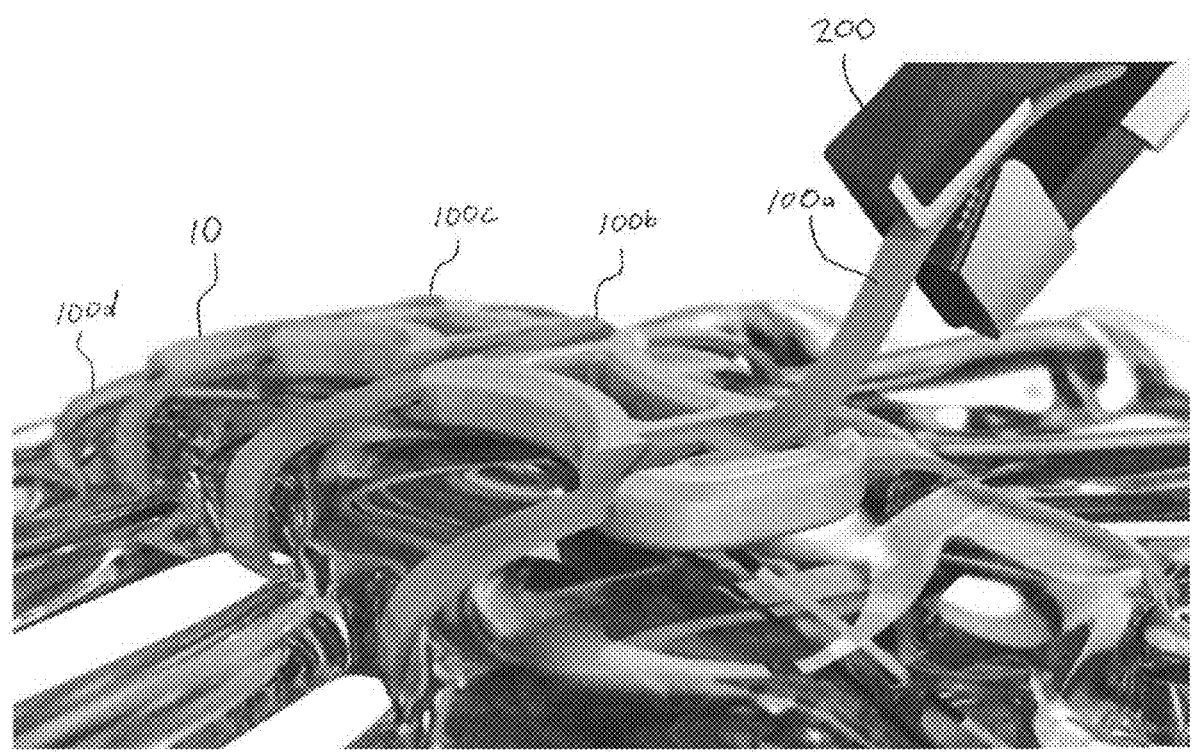
FIG. 15 is a perspective view of a system and method for sternum fixation in accordance with the present disclosure.
Figure 16:
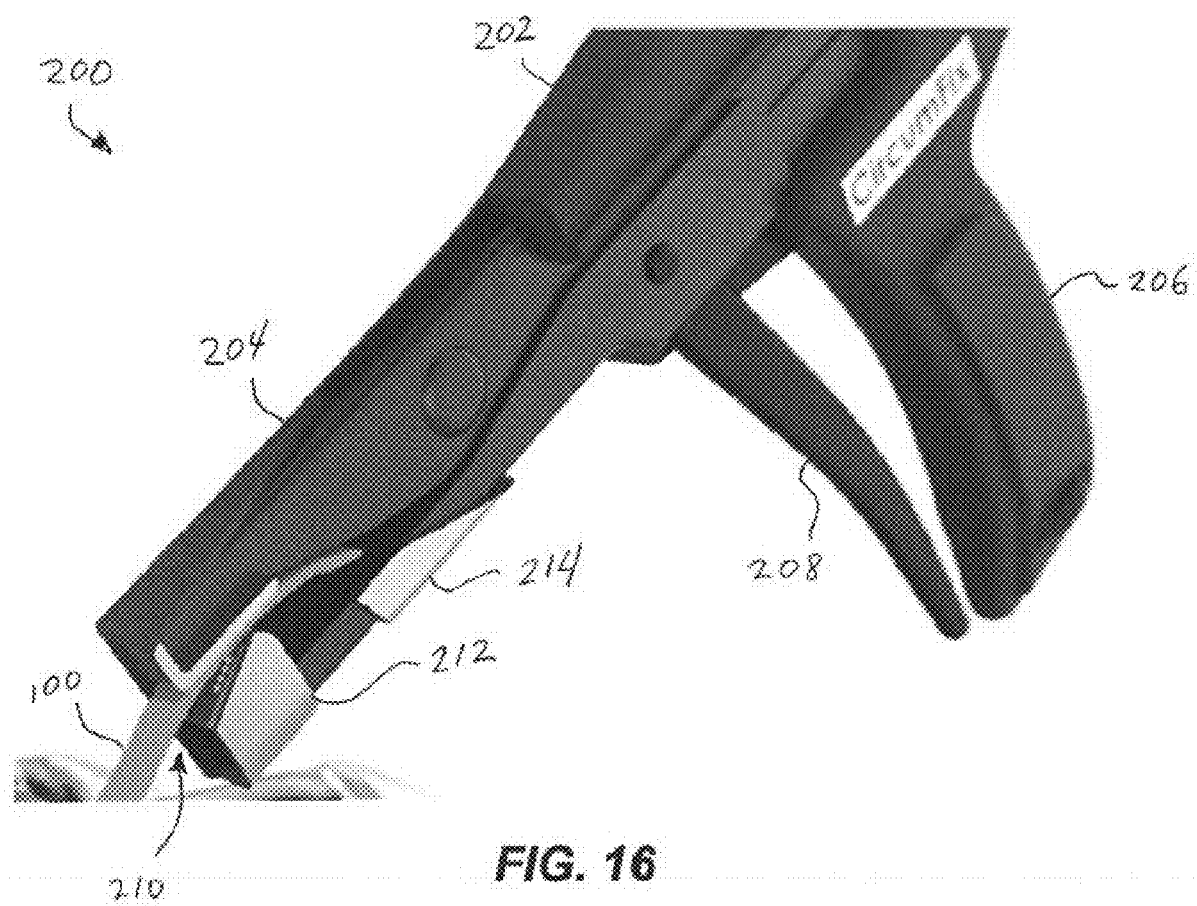
FIG. 16 is a perspective view of an embodiment of a handheld tensioning and cutting device configured to tension and cut bands on a sternum fixation device.

Referring to FIG. 15 and FIG. 16, an embodiment of a system and method for sternum fixation are illustrated. As shown in FIG. 15, a plate 10 is placed against a fractured or surgically cut sternum. One or more bands 100a, 100b, 100c, 100d are positioned on plate 10, and each band includes a strap extending from a first lateral side of the band, passing around the sternum and back into the second lateral edge of the band into the head. The free end of the band then passes through the latch on the head, and out of the head. The free end may then be inserted into the aperture on the end of a tensioning and cutting tool 200. The free end is pulled to a predetermined tension and trimmed flush with the head, as shown in items 100b and 100c in FIG. 15. Such method provides consistent tightening of each band in a precise, repeatable and quick manner.

Referring to FIG. 16, an embodiment of a handheld tool for tensioning and trimming bands is shown. Tool 200 includes a body 202 having a barrel 204 and a hand grip, or handle 206. An actuating lever 208 is positioned near the handle 206. During use, a user may grasp handle 206 and use one or more fingers of the gripping hand to depress an actuator lever 208. Movement of actuator lever 208 engages a linkage along the length of barrel 204, causing one or more jaws 212 to grip onto a band 100 inserted through an aperture 210 in the distal end of the barrel 204.

The gripping jaws 212 pull on band 100 and tighten band 100 to a predetermined tension associated with placement of a travel limiter 214 in some embodiments. When the predetermined tension is reached, the band 100 is trimmed neatly flush with the head 110. After a first band is tightened and cut, the user will then tighten and cut additional bands on the plate until all bands are tightened and cut in a similar manner, each to a desired tension. In some embodiments, the tension applied to each band is the same. In further embodiments, the tension applied to each band may be customized for that particular band.

Figure 17:
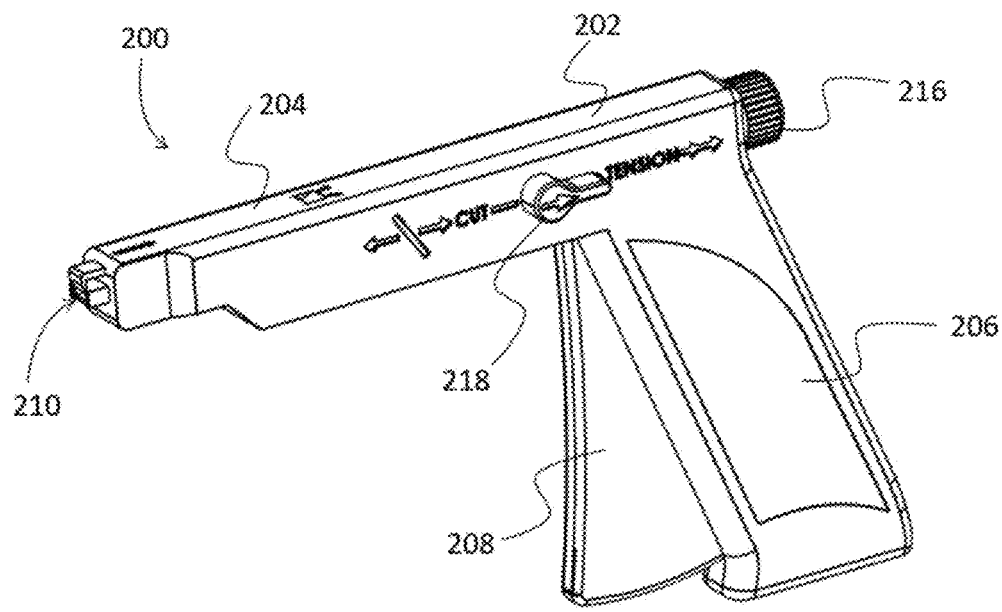
FIG. 17 is a perspective view of an embodiment of a handheld tensioning and cutting device configured to tension and cut bands on a sternum fixation device.

In various other embodiments, such as the one shown in FIG. 17, tool 200 may take on the form of a "trigger-pull" shaped similarly to a handgun. Tool 200 includes a rotatable knob 216 located on the end of the tool 200 opposite the aperture 210. When twisted, rotatable knob 216 operates to adjust the tension settings such that a desirable amount of tension in band 100 can be obtained when a user depresses the actuator lever. Further, a switch 218 may also be included, switch 218 enabling tool 200 to alternate between a tensioning mode and a cutting mode. With switch 218 set in a tensioning mode, tool 200 operates to tighten the band 100 being fed through the aperture 210 on the distal end of the barrel 204 when a user squeezes and depresses the actuating lever 208. Once the tension in band 100 reaches a desirable or pre-determined level, the user can then adjust the setting of the switch 218 to change from the tensioning mode to the cutting mode, whereby the user, by depressing actuating lever 208, can cut the tensioned band 100, such that band 100 is neatly flush with head 110.

Figure 18:
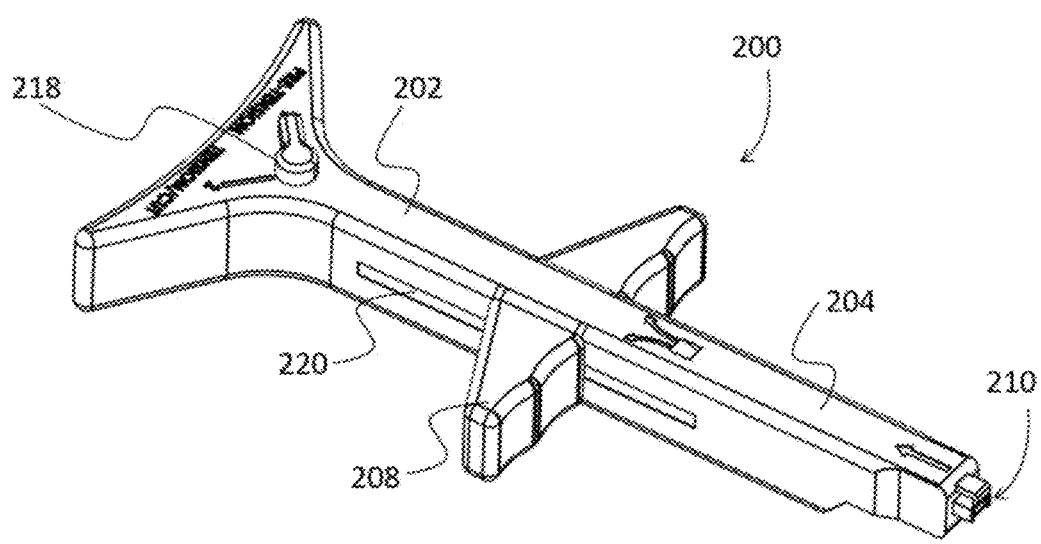
FIG. 18 is a perspective view of an embodiment of a handheld tensioning and cutting device configured to tension and cut bands on a sternum fixation device.

In another embodiment, such as that of FIG. 18, tool 200 can take the form of a "linear-pull" mechanism shaped similarly to a syringe. In such an embodiment, actuator lever 208 takes on a more linear movement profile and functions to tension band 100 when the user pulls the lever 208 backwards along slider track 220 in a direction away from aperture 210. Once band 100 reaches the prerequisite tension levels, switch 218 is utilized to change tool 200 from the tensioning mode to a cutting mode. When in the cutting mode, the user can cut the tensioned band 100 by pulling lever 208 back along the slider track 220, and the band 100 will be cut such that it is neatly flush with head 110. In some embodiments, tool 200 is a highly intuitive, disposable single-use tool.

Figure 19A:
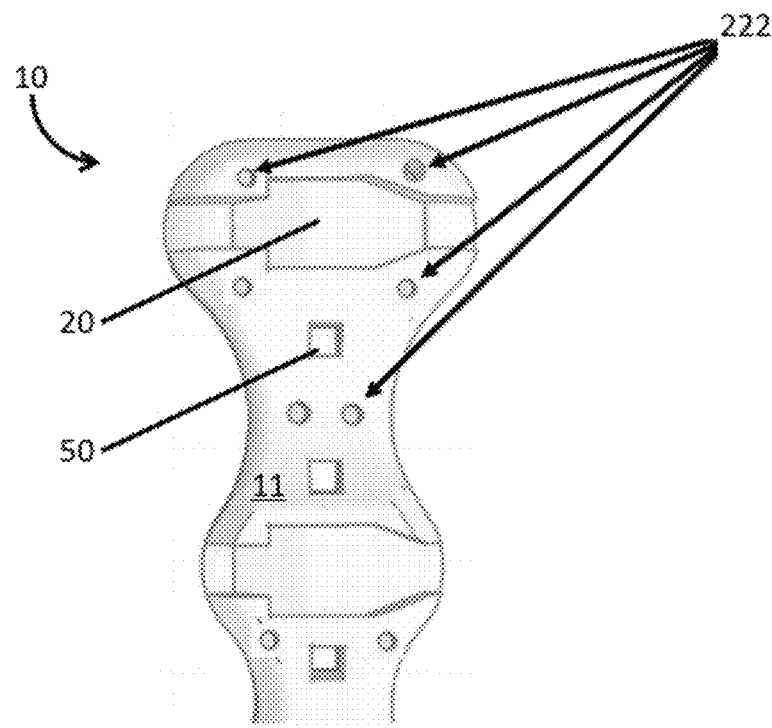
FIGS. 19A and 19B are a front and bottom side perspective view of a sternum fixation device in accordance with the present disclosure.
Figure 19B:
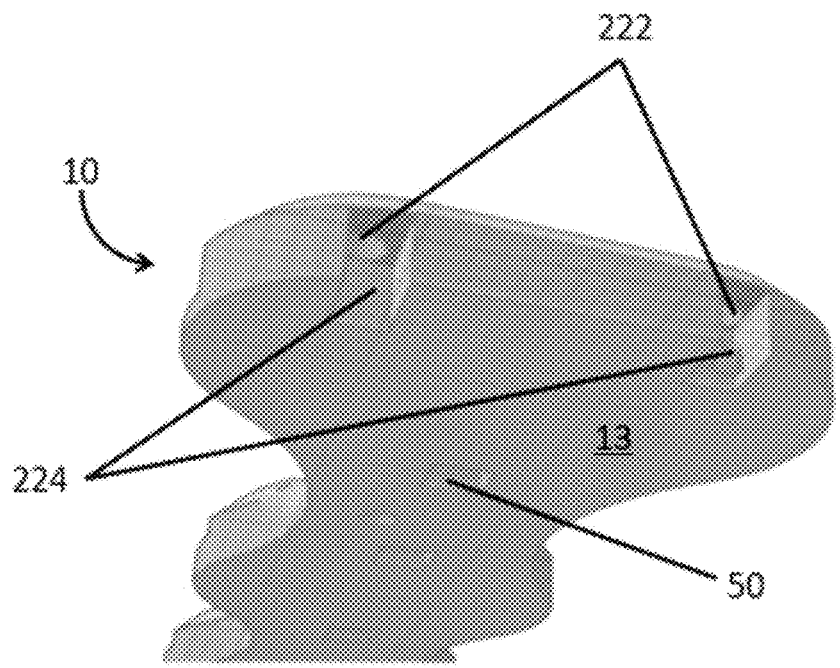

Referring now to FIG. 19A and FIG. 19B, in some embodiments, the plate 10 may include a plurality of suture holes 222 defined through the plate 10, from the outer side 11 to the inner side 13. Each of the plurality of suture holes 222 are configured to accommodate a suture needle, suture, wire, fiber wire, or another similarly sized medical device and can be used to secure hard tissue, soft tissue, or other devices. For example, in some applications, the user can utilize suture holes 222 to help mount a wireless pacemaker or other electronic device to the sternum of a patient. In other embodiments, in addition to the plurality of suture holes 222, the plate 10 may include a plurality corresponding undercuts 224. Undercuts 224 are defined on the inner side 13 of plate 10 in a location directly corresponding to that of the suture holes 222. Undercuts 224 allow for the user to more easily manipulate the suture needle or other medical device as it passes through the suture hole 222 to the inner side 13 of the plate 10. Thus, in addition to the primary attachment means of utilizing the interlocking bands 100 and sockets 20, suture holes 222 provide a secondary means of attaching plate 10 to a patient's sternum.

Figure 20A:
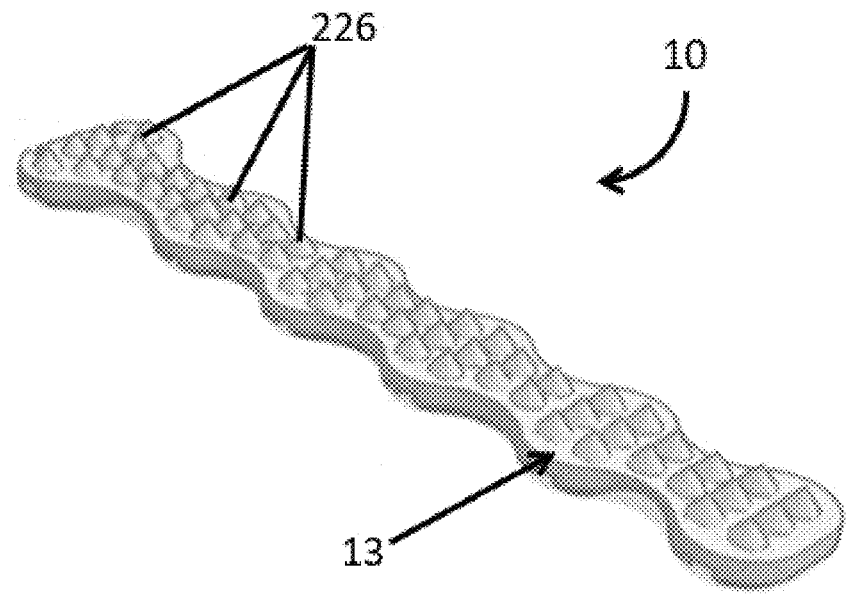
FIGS. 20A and 20B are a bottom side and a lateral side perspective view of a sternum fixation device in accordance with the present disclosure.
Figure 20B:
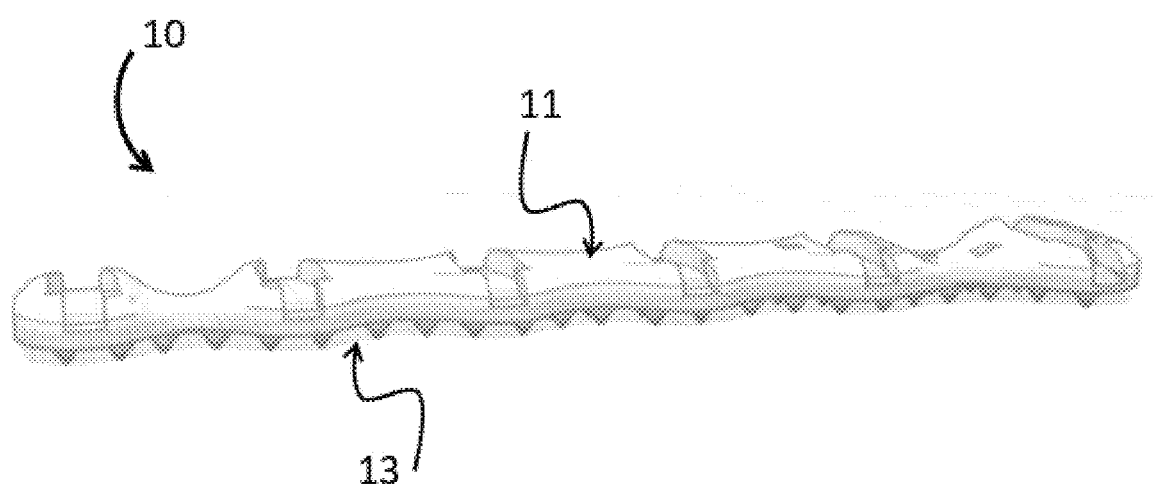

In some embodiments, the inner side 13 of plate 10 is a smooth surface. However, in further embodiments, such as those seen in FIG. 20A and FIG. 20B, inner side 13 of plate 10 may instead comprise a textured surface 226. The texture 226 of the inner side 13 can take the shape of spikes, as seen in the FIGS. 20A and 20B, or can comprise stubs, posts, or any other structure protruding from the inner side 13 of plate 10. Regardless of its structure, texture 226 will always serve at least two purposes. First, texture 226 limits the total contact surface area between plate 10 and the underlying bone of the patient. Second, texture 226 provides enhanced traction which helps prevent the plate 10 from slipping around when placed on top of the underlying bone.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative aspects. Accordingly, all such modifications are intended to be included within the scope of the present disclosure as defined in the appended claims.

The foregoing description of aspects of the invention aspect has been presented for purposes of illustration and description. It is not intended to be exhaustive or to limit the disclosure to the precise form disclosed, and modifications and variations are possible in light of the above teachings or may be acquired from this disclosure. The aspects were chosen and described in order to explain the principals of the disclosure and its practical application to enable one skilled in the art to utilize the various aspects and with various modifications as are suited to the particular use contemplated. Other substitutions, modifications, changes and omissions may be made in the design, operating conditions and arrangement of the aspects without departing from the scope of the present disclosure as expressed in the appended claims.

What is claimed is:

1. An apparatus for sternum fixation, comprising:
   a plate comprising a first end and a second end, a right lateral edge and a left lateral edge, an inner side configured for placement against the sternum, and an outer side configured to face away from the sternum;
   a first lobe disposed on the plate at the first end, the first lobe including a band socket defined as a blind recess in the outer side of the plate, the band socket including a right lateral stop and a left lateral stop opposite the right lateral stop;
   a right lateral channel defined in the first lobe from the right lateral edge to the band socket, the right lateral channel defined above a right side floor in the socket; and
   a left lateral channel opposite the right lateral channel defined in the first lobe from the left lateral edge to the band socket, the left lateral channel defined above a left floor in the socket,
   wherein the left lateral stop protrudes from the left lateral channel inwardly into the socket at an inclined angle above the left floor forming a wedge-shaped recess in the socket, and
   wherein the right lateral stop comprises first and second tapered walls extending upwardly from the right floor in the socket toward the right lateral channel.

2. The apparatus of claim 1, further comprising:
   a second lobe disposed on the plate longitudinally spaced from the first lobe; and
   a first bridge disposed between the first lobe and the second lobe.

3. The apparatus of claim 2, further comprising a first clearance hole defined through the plate on the first bridge between the first and second lobes.

4. The apparatus of claim 3, further comprising a second band socket defined in the second lobe as a blind recess in the outer side of the plate.

5. The apparatus of claim 4, further comprising:
   a third lobe disposed on the plate longitudinally spaced from the first and second lobes; and
   a second bridge disposed between the second lobe and the third lobe.

6. The apparatus of claim 5, further comprising a second clearance hole defined through the plate on the second bridge between the second and third lobes.

7. The apparatus of claim 6, further comprising a third band socket defined in the third lobe as a blind recess in the outer side of the plate.

8. The apparatus of claim 7, further comprising:
   a fourth lobe disposed on the plate longitudinally spaced from the first, second and third lobes; and
   a third bridge disposed between the third lobe and the fourth lobe.

9. The apparatus of claim 8, further comprising a third clearance hole defined through the plate on the third bridge between the third and fourth lobes.

10. The apparatus of claim 9, further comprising a fourth band socket defined in the fourth lobe as a blind recess in the outer side of the plate.

11. The apparatus of claim 10, further comprising:
    a fifth lobe disposed on the plate longitudinally spaced from the first, second, third and fourth lobes; and
    a fourth bridge disposed between the fourth lobe and the fifth lobe.

12. The apparatus of claim 11, further comprising a fourth clearance hole defined through the plate on the fourth bridge between the fourth and fifth lobes.

13. The apparatus of claim 12, further comprising a fifth band socket defined in the fifth lobe as a blind recess in the outer side of the plate.

14. The apparatus of claim 13, further comprising a fastener band disposed on the plate, the fastener band including a head disposed in the first band socket and a strap extending from the head out of the right lateral channel away from the plate.

15. The apparatus of claim 14, wherein the strap is configured to extend around the sternum, through the right left lateral channel into the head disposed in the socket.

16. The apparatus of claim 15, further comprising:
    an arcuate recess defined on the inner side of the plate between the first and second lobes.

17. The apparatus of claim 16, further comprising a living hinge formed in the first bridge adjacent the arcuate recess configured to allow the first lobe to flex inwardly relative to the second lobe to accommodate the curvature of the sternum toward a manubrium of the sternum.

* * * * *